United States Patent [19]

Cordier et al.

[11] 4,418,213

[45] Nov. 29, 1983

[54] PROCESS FOR THE SELECTIVE PREPARATION OF META-CHLOROANILINES

[75] Inventors: Georges Cordier, Francheville; Pierre Fouilloux, Caluire, both of France

[73] Assignee: Rhone-Poulenc Agrochimie, Lyons, France

[21] Appl. No.: 283,151

[22] Filed: Jul. 14, 1981

[30] Foreign Application Priority Data

Aug. 1, 1980 [FR] France .................................. 80 17324
Sep. 26, 1980 [FR] France .................................. 80 20979

[51] Int. Cl.³ ........................ C07C 85/11; C07C 85/24
[52] U.S. Cl. ................................... 564/412; 564/305; 564/309; 564/315; 564/330; 564/417
[58] Field of Search ............... 564/305, 315, 412, 417, 564/309, 330

[56] References Cited

U.S. PATENT DOCUMENTS 4,085,141 4/1978 Wedemeyer et al. ............... 564/412

OTHER PUBLICATIONS

Royals, "Advanced Organic Chemistry", pp. 467–469 (1954).

*Primary Examiner*—Robert V. Hines
*Attorney, Agent, or Firm*—Browdy and Neimark

[57] ABSTRACT

Process for the selective preparation of meta-chloroanilines.

It is carried out by the hydrodechlorination of polychloroanilines or polychloronitrobenzenes with hydrogen, in the liquid phase, under the action of heat, at atmospheric pressure or under pressure, in the presence of a noble metal, in an anhydrous organic medium and in the presence of a Lewis acid.

These meta-chloroanilines are intermediates especially for active plant-protection substances.

20 Claims, No Drawings

PROCESS FOR THE SELECTIVE PREPARATION OF META-CHLOROANILINES

The present invention relates to a process for the preparation of anilines substituted by chlorine in the meta-position, by reacting hydrogen with nitrogen-containing aromatic compounds which are more highly halogen-substituted. These meta-chloroanilines are intermediates especially for the manufacture of plant-protection products.

The preparation of chloroanilines substituted in the meta-position by reacting polychloroanilines with hydrogen under pressure, in an acid medium, especially an aqueous acid medium, in the presence of a catalyst based on a noble metal, has been described in French Pat. No. 2,298,531, corresponding to U.S. Pat. No. 4,085,141. However, the process described requires the use of high pressures and very large amounts of hydrochloric acid, which presents serious corrosion problems.

The object of the present invention is precisely to prepare meta-substituted chloroanilines by the selective hydrodechlorination of polychloroanilines or polychlorobenzenes, without a corrosion problem.

The invention relates more particularly to a process for the preparation of anilines substituted in the meta-position by chlorine, by the catalytic hydrogenation, in the liquid phase, under the action of heat and under pressure in the presence of noble metals from group VIII of the periodic classification, of nitrogen-containing and chlorine containing benzene derivatives of the formula:

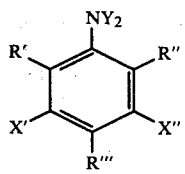

in which: Y represents the hydrogen atom or the oxygen atom, X' and X", which are identical to or different from one another, each represent a chlorine atom or an optionally substituted alkyl, aryl, aralkyl, alkoxy or aralkoxy radical, at least one of the symbols X' and X" necessarily being a chlorine atom and it being furthermore possible for one of the symbols X' and X" to be hydrogen, and R', R" and R'", which are identical to or different from one another, each represent a chlorine atom or an optionally substituted alkyl, aralkyl, alkoxy or aryloxy radical, at least one of these three symbols representing the chlorine atom and it being furthermore possible for at most two of the symbols R', R" and R'" to be hydrogen, in which process the reaction is carried out in an essentially anhydrous medium, in the presence of a catalytic amount of at least one Lewis acid as a catalyst.

The term "Lewis acid" is to be understood as meaning compounds having an electron-deficient central atom which captures the electrons of atoms such as halogens. The preferred compounds are chlorides, bromides, iodides or even fluorides of elements such as boron, aluminium, gallium, tin, phosphorus, arsenic, antimony, bismuth, titanium, zirconium, molybdenum, manganese, iron, cobalt, nickel, copper, zinc and cadmium.

It has been observed in particular that valuable results are obtained using aluminium chloride and bromide, stannous and stannic chlorides, ferric chloride, zinc chloride and bromide, cuprous chloride and nickel chloride as catalysts, particularly advantageous results being obtained using aluminium chloride or bromide.

For the purpose of the invention, the term "catalytic amount" is understood as meaning an amount which is such that the molar ratio of the Lewis acid to the starting nitrogen-containing and chlorine-containing benzene derivative is between 0.0001 and 1 and preferably between 0.01 and 0.5.

The process according to the invention is carried out in the liquid phase (except, of course, for the catalyst based on a noble metal). This liquid phase is organic and essentially anhydrous. It is preferably homogeneous, it being possible for the medium to consist of the starting nitrogen-containing and chlorine-containing benzene product in the molten state (for Y=H) or of a solution of this product in an essentially anhydrous organic solvent which is inert under the reaction conditions, this solvent preferably having a high b.p., such as an aliphatic solvent like cyclohexane and dodecane, or an aromatic solvent such as chlorobenzene and polychlorobenzenes. The latter, in particular, are not hydrochlorinated under the reaction conditions. The liquid phase can also be heterogeneous and consist of a two-phase liquid medium.

The pressure at which the reaction is carried out can be chosen within a wide range. Although it is to no advantage, the reaction can be carried out under reduced pressure, e.g. in a solvent medium under reflux. However, the reaction is preferably carried out at a pressure which is at least equal to atmospheric pressure. Working at atmospheric pressure makes it possible to supply the hydrogen in the form of a stream at an adjustable rate.

If the reaction is carried out under pressure, the pressure is generally above 3 bars (relative pressure) and preferably above 5 bars. There is no critical upper limit to the pressure, but, for economic reasons, the reaction is advantageously carried out at pressures below 100 bars, pressures below 20 bars being preferred.

The reaction temperature is generally between 90° and 300° C., preferably between 110° and 200° C. In the case where relatively volatile Lewis acids are used, an elevated temperature can lead to the existence of a relatively high partial pressure for the compounds, other than hydrogen, in the vapour phase (the term "vapour phase" is obviously to be understood as meaning the vapour phase surmounting the liquid reaction medium).

The nobel metals forming the base of the catalysts used in the invention are metals from group VIII of the periodic classification, such as ruthenium, rhodium, palladium, osmium, iridium and platinum; palladium is the preferred metal. The metal can be in the metallic form or in the form of a chemical compound; in general, the metal is preferably used in the metallic form.

The catalyst can be supported or unsupported. Any support which is in itself known for supporting catalysts can be used as the catalyst support, provided that this support is resistant to the medium and to acids; more particularly suitable supports which may be mentioned are active charcoal, alumina, silica and barium sulphate; active charcoal is a preferred support. The catalyst and its support are advantageously in a finely divided form;

specific surface areas of more than 100 m²/g are generally suitable.

The amount of catalyst used is such that the proportion by weight of noble metal of the catalyst, relative to the compound of the formula (I) to be treated, is generally between 0.01 and 10%, preferably between 0.1 and 5%.

Furthermore, the noble metal can be used in association with another metal which is co-deposited with it onto the support. This second metal belongs to groups Ib to Va of the periodic classification. Bismuth, lead, tin, thallium, mercury and silver may be mentioned in particular. The Applicant Company has found, in particular, that good results are obtained using silver.

The following may preferably be mentioned as compounds of the formula (I) which are capable of being treated by the process of the invention: 2,3-dichloronitrobenzene and 2,3-dichloroaniline; 2,5-dichloronitrobenzene and 2,5-dichloroaniline; 3,4-dichloronitrobenzene and 3,4-dichloroaniline; 2,3,4-trichloronitrobenzene and 2,3,4-trichloroaniline; 2,3,5-trichloronitrobenzene and 2,3,5-trichloroaniline; 2,3,6-trichloronitrobenzene and 2,3,6-trichloroaniline; 2,4,5-trichloronitrobenzene and 2,4,5-trichloroaniline; 3,4,5-trichloronitrobenzene and 3,4,5-trichloroaniline; 2,3,4,6-tetrachloronitrobenzene and 2,3,4,6-tetrachloroaniline; 2,3,4,5-tetrachloronitrobenzene and 2,3,4,5-tetrachloroaniline; 2,3,5,6-tetrachloronitrobenzene and 2,3,5,6-tetrachloroaniline; and pentachloronitrobenzene and pentachloroaniline; the following may also be mentioned: 4,5,6-trichloro-2-methylnitrobenzene and 4,5,6-trichloro-2-methylaniline; 2,5-dichloro-4-methylnitrobenzene and 2,5-dichloro-4-methylaniline; 2,3,5,6-tetrachloro-4-methylnitrobenzene and 2,3,5,6-tetrachloro-4-methylaniline; 2,5-dichloro-3,4-dimethylnitrobenzene and 2,5-dichloro-3,4-dimethylaniline; 2,5-dichloro-4-ethylnitrobenzene and 2,5-dichloro-4-ethylaniline; 2,5-dichloro-4-propylnitrobenzene and 2,5-dichloro-4-propylaniline; 3,4,6-trichloro-2-benzylnitrobenzene and 3,4,6-trichloro-2-benzylaniline; 2,2'-dinitro-3,5,6,3',5',6'-hexachlorodiphenylmethane and 2,2'-diamino-3,5,6,3',5',6'-hexachlorodiphenylmethane; 2-nitro-3,4,5-trichlorobiphenyl and 2-amino-3,4,5-trichlorobiphenyl; 4,4'-dinitrooctachlorobiphenyl and 4,4'-diaminooctachlorobiphenyl; 4,5-dichloro-2-methoxynitrobenzene and 4,5-dichloro-2-methoxyaniline; 3,4-dichloro-2-methoxynitrobenzene and 3,4-dichloro-2-methoxyaniline; 3,6-dichloro-2-methoxynitrobenzene and 3,6-dichloro-2-methoxyaniline; 5,6-dichloro-2-methoxynitrobenzene and 5,6-dichloro-2-methoxyaniline; 3,4,6-trichloro-2-methoxynitrobenzene and 3,4,6-trichloro-2-methoxyaniline; 3,4,5-trichloro-2-methoxynitrobenzene and 3,4,5-trichloro-2-methoxyaniline; 3,4,5,6-tetrachloro-2-methoxynitrobenzene and 3,4,5,6-tetrachloro-2-methoxyaniline; 4,5-dichloro-3-methoxynitrobenzene and 4,5-dichloro-3-methoxyaniline; 5,6-dichloro-3-methoxynitrobenzene and 5,6-dichloro-3-methoxyaniline; 2,5-dichloro-3-methoxynitrobenzene and 2,5-dichloro-3-methoxyaniline; 4,5,6-trichloro-3-methoxynitrobenzene and 4,5,6-trichloro-3-methoxyaniline; 2,4,5,6-tetrachloro-3-methoxynitrobenzene and 2,4,5,6-tetrachloro-3-methoxyaniline; 2,3-dichloro-4-methoxynitrobenzene and 2,3-dichloro-4-methoxyaniline; 2,5-dichloro-4-methoxynitrobenzene and 2,5-dichloro-4-methoxyaniline; 2,3,6-trichloro-4-methoxynitrobenzene and 2,3,6-trichloro-4-methoxyaniline; 2,3,5-trichloro-4-methoxynitrobenzene and 2,3,5-trichloro-4-methoxyaniline; 2,3,5,6-tetrachloro-4-methoxynitrobenzene and 2,3,5,6-tetrachloro-4-methoxyaniline; 4,5-dichloro-2-phenoxynitrobenzene and 4,5-dichloro-2-phenoxyaniline; 3,4,5,6-tetrachloro-2-phenoxynitrobenzene and 3,4,5,6-tetrachloro-2-phenoxyaniline; 2,4,5,6-tetrachloro-3-phenoxynitrobenzene and 2,4,5,6-tetrachloro-3-phenoxyaniline; 2,5-dichloro-4-phenoxynitrobenzene and 2,5-dichloro-4-phenoxyaniline; and 2,3,5,6-tetrachloro-4-phenoxynitrobenzene and 2,3,5,6-tetrachloro-4-phenoxyaniline.

The following may preferably be mentioned amongst the anilines, substituted in the meta-position by a chlorine atom, which are capable of being prepared by the process according to the invention: meta-chloroaniline and 3,5-dichloroaniline; the following may also be mentioned: 5-chloro-2-methylaniline, 5-chloro-3-methylaniline, 3-chloro-4-methylaniline, 3,5-dichloro-4-methylaniline, 5-chloro-3,4-dimethylaniline, 3-chloro-4-ethylaniline, 3-chloro-2-benzylaniline, 4,4'-diamino-2,6,2',6'-tetrachlorobiphenyl, 3-chloro-2-methoxyaniline, 5-chloro-2-methoxyaniline, 3,5-dichloro-2-methoxyaniline, 3-chloro-4-methoxyaniline, 5-chloro-3-methoxyaniline, 3,5-dichloro-4-methoxyaniline, 3-chloro-2-phenoxyaniline, 5-chloro-2-phenoxyaniline, 3,5-dichloro-2-phenoxyaniline and 3,5-dichloro-4-phenoxyaniline.

The process according to the invention can be carried out continuously or batchwise. At the end of the reaction, the catalyst can be separated off, if appropriate, by filtration or by equivalent means such as centrifugation; the meta-chloroaniline prepared can be separated off by any means which is in itself known, e.g. by solvent extraction and/or by distillation.

The process according to the invention is very advantageous because it makes it possible to obtain meta-chloroanilines under excellent conditions of selectivity, at moderate temperatures and under moderate pressures, without the problems of substantial corrosion and of premature wear on the equipment.

The following examples, which are given without implying a limitation, illustrate the manner in which the process according to the invention is carried out and the results obtained.

EXAMPLE 1

2,3,4,5-Tetrachloroaniline (1.16 g), a catalyst consisting of palladium deposited on active charcoal (specific surface area of the carbon black: 1,300 m²/g; proportion by weight of palladium: 10%) (0.4 g), anhydrous cyclohexane (17 cc) and a 5% strength (weight/volume) solution of aluminium bromide (AlBr$_3$) in anhydrous cyclohexane (3 cc) are introduced into a 70 cc tantalum-lined autoclave.

The autoclave is closed and purged first with argon and then with hydrogen. Hydrogen is then introduced under a pressure of 10 bars and the autoclave is isolated and heated to 160° C., whilst allowing the autogenous pressure to increase to a total (relative) pressure of 21 bars. The reaction is allowed to proceed under these conditions for 4 hours 30 minutes.

The autoclave is cooled. The contents of the autoclave are filtered in order to separate the solid catalyst from the hexane solution. The latter is then washed with an aqueous solution of sodium hydroxide (NaOH) so as totally to neutralise the hydrochloric acid produced by the reaction.

After distillation of the cyclohexane, 3,5-dichloroaniline is obtained with a yield of 99.5%.

EXAMPLE 2

The reaction is carried out as in Example 1, the following amounts being introduced: 2,3,4,5-tetrachloroaniline (1.16 g), a catalyst consisting of palladium deposited at a rate of 5% by weight on the same active charcoal as in Example 1 (0.4 g), anhydrous stannous chloride (0.095 g, i.e. 0.082 part per part of 2,3,4,5-tetrachloroaniline) and cyclohexane (20 cc).

3,5-Dichloroaniline is obtained with a yield of 96.5%.

EXAMPLE 3

The reaction is carried out as in Example 1, the following amounts being introduced: 2,3,4,5-tetrachloroaniline (1 g), the catalyst used in the previous example (0.3 g) and anhydrous stannous chloride (0.64 g). The latter is dissolved in the molten aniline at the reaction temperature (160° C.). The reaction lasts 3 hours 20 minutes.

Under these conditions, 3,5-dichloroaniline is obtained with a yield of 100%.

EXAMPLE 4

The reaction is carried out as in Example 2, the stannous chloride being replaced by zinc iodide (0.32 g). The reaction lasts 10 hours.

Under these conditions, 3,5-dichloroaniline is obtained with a yield of 98.2%.

EXAMPLES 5 TO 13

2,3,4,5-Tetrachloroaniline (TTCA) (1 g), a catalyst containing 3% of palladium and 2% of silver codeposited on active charcoal having a specific surface area of about 1,300 m$^2$/g (0.3 g) and a variable amount of a Lewis acid, as a catalyst, are introduced into a 70 cc tantalum-lined autoclave.

The reaction is carried out at 160° C. under 21 bars. The treatment of the reaction medium after the reaction is carried out as in Example 1.

The table below indicates the reaction time and the yield of 3,5-dichloroaniline for each Lewis acid and for a given molar ratio Lewis acid/tetrachloroaniline (LA/TTCA).

| Example | Lewis acid | LA/TTCA | Time | | Yield of 3,5-DCA |
|---|---|---|---|---|---|
| 5 | SnCl$_2$ | 1.0 | 3 hours | | 100% |
| 6 | SnCl$_4$ | 1.0 | 13 hours | | 100% |
| 7 | AlCl$_3$ | 0.6 | 3 hours | 5 minutes | 95.6% |
| 8 | AlCl$_3$ | 0.2 | 9 hours | 20 minutes | 92.5% |
| 9 | AlBr$_3$ | 0.02 | 6 hours | 15 minutes | 100% |
| 10 | FeCl$_3$ | 1.0 | 13 hours | | 100% |
| 11 | ZnCl$_2$ | 1.0 | 9 hours | 20 minutes | 95.0% |
| 12 | CuCl | 1.0 | 10 hours | 40 minutes | 100% |
| 13 | NiCl$_2$ | 1.0 | 15 hours | 50 minutes | 100% |

EXAMPLE 14

The reaction is carried out as in Example 1, the 2,3,4,5-tetrachloroaniline being replaced by an equal amount of 2,3,5,6-tetrachloroaniline. The reaction lasts 13 hours.

Under these conditions, 3,5-dichloroaniline is obtained with a yield of 99.6%.

EXAMPLE 15

The reaction is carried out as in Example 1, the 2,3,4,5-tetrachloroaniline being replaced by 3,4,5-trichloroaniline (0.985 g), the Lewis acid being added in the form of a 10% strength w/v cyclohexane solution (1 cc) and the same palladium catalyst (0.05 g) being used.

The reaction is carried out for 120 minutes.

Under these conditions, 3,5-dichloroaniline is obtained with a yield of 86%.

EXAMPLE 16

3,4,5-Trichloroaniline (10 g; 0.05 mol), zinc iodide (ZnI$_2$) (0.4 g; 1.25×10$^{-3}$ mol), a catalyst containing 5% of palladium on active charcoal (0.5 g) and 3,5-dichloroaniline (56.5 g; 0.35 mol) are introduced into a 250 ml reactor equipped with a central stirrer rotating at 1,000 rpm, a condenser, a thermometer and a gas inlet.

Hydrogen is then introduced as in Example 1, except that the total pressure is 20 bars and that the heating is carried out at 180° C. for two hours.

Under these conditions, all the 3,4,5-trichloroaniline is converted and 3,5-dichloroaniline is obtained with a yield of 100%.

EXAMPLE 17

3,4,5-Trichloroaniline (2 g; about 0.01 mol), aluminium bromide (AlBr$_3$) (0.6 g; 2.25×10$^{-3}$ mol), a catalyst containing 5% of palladium on active charcoal (0.8 g) and dodecane (20 ml) are introduced into a round-bottomed flask of 100 ml capacity, fitted with a central stirrer rotating at 1,000 rpm, a condenser, a thermometer and a gas inlet.

A temperature of 160° C. is maintained and a stream of hydrogen is passed in at a rate of 6 liters/hour, for 30 minutes, at atmospheric pressure.

The reaction mixture is subsequently treated with water and then ether. The catalyst and then the water are separated off. The solvents are removed by distillation.

Under these conditions, 3,5-dichloroaniline is obtained with a yield of 99.5%. The degree of conversion of the 3,4,5-trichloroaniline is 100%.

EXAMPLE 18

The reaction is carried out as in the previous example, in a 250 ml reactor equipped in the same manner, the following amounts being introduced: 3,4,5-trichloroaniline (19.7 g; 0.1 mol), aluminium bromide (AlBr$_3$) (3.0 g; 1.12×10$^{-2}$ mol), the catalyst containing 5% of palladium on active charcoal (0.5 g) and 1,2,4-trichlorobenzene (60 ml).

Whilst the reaction medium is being stirred, a temperature of 160° C. and a stream of hydrogen of 27 liters/hour are maintained for 4 hours.

By following the procedure of the previous example, 3,5-dichloroaniline is obtained with a yield of 100%.

I claim:

1. A process for the preparation of anilines substituted in the meta-position by chlorine, by the catalytic hydrogenation, in the liquid phase, under the action of heat and under pressure, in the presence of noble metals from group VIII of the periodic classification, of nitrogen-containing and chlorine-containing benzene derivatives of the formula:

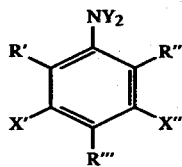 (I)

in which: Y represents the hydrogen atom or the oxygen atom, X' and X", which are identical to or different from one another, each represent a chlorine atom, or an optionally substituted alkyl, aryl, aralkyl, alkoxy or aralkoxy radical, at least one of the symbols X' and X" necessarily being a chlorine atom and it being furthermore possible for one of the symbols X' and X" to be hydrogen, and R', and R" and R''', which are identical to or different from one another, each represent a chlorine atom or an optionally substituted alkyl, aralkyl, alkoxy or aryloxy radical, at least one of these three symbols representing the chlorine atom and it being furthermore possible for at most two of the symbols R', R" or R''' to be hydrogen, in which process the reaction is carried out in an essentially anhydrous medium at between 90° and 300° C., in the presence of a catalytic amount of at least one Lewis acid as a catalyst, wherein the Lewis acid is a halide of an element selected from the group consisting of boron, aluminum, gallium, tin, phosphorus, arsenic, antimony, bismuth, titanium, zirconium, molybdenum, manganese, iron, cobalt, nickel, copper, zinc and cadmium, wherein the molar ratio of the Lewis acid to the starting nitrogen-containing and chlorine-containing benzene derivative is between 0.0001 and 1.

2. A process according to claim 1, wherein the reaction is carried out in the presence of a catalytic amount of a compound chosen from the group comprising aluminium chloride and bromide, stannous and stannic chlorides, ferric chloride, zinc chloride and iodide, cuprous chloride and nickel chloride.

3. A process according to claim 1, wherein the molar ratio of the Lewis acid to the starting nitrogen-containing and chlorine-containing benzene derivative is between 0.01 and 0.5.

4. A process according to claim 1, 2 or 3, wherein Y=H and the reaction is carried out in the molten starting material.

5. A process according to claim 1, 2 or 3, wherein the reaction is carried out in solution in an organic solvent.

6. A process according to claim 1, 2 or 3, wherein R', R", R''', X' and X", which are identical to or different from one another, represent the hydrogen atom or the chlorine atom.

7. A process for the preparation of optionally substituted meta-dichloroanilines, according to claim 1, wherein X' and X" represent the chlorine atom.

8. A process for the preparation of optionally substituted meta-monochloroanilines, according to claim 1, wherein only one of the two radicals X' and X" is the chlorine atom.

9. A process for the preparation of 3,5-dichloroaniline, according to claim 1, wherein: Y is the hydrogen or oxygen atom, X' and X" are the chlorine atom and R', R" and R''' are the hydrogen atom or the chlorine atom, at least one of them being the chlorine atom.

10. A process according to claim 1, wherein the reaction medium only contains a liquid phase, except for the catalyst based on a noble metal.

11. A process according to claim 1, wherein the reaction is carried out at a pressure below 3 bars.

12. A process according to claim 11, wherein the reaction is carried out at atmospheric pressure.

13. A process according to claim 1, wherein the total pressure is between 3 and 100 bars.

14. A process according to claim 13, wherein the total pressure is between 5 and 20 bars.

15. A process according to claim 1, wherein the catalyst is palladium.

16. A process according to claim 1, wherein the proportion by weight of noble metal, relative to the compound of the formula (I), is between 0.01 and 10%.

17. A process according to claim 1, wherein the reaction is carried out in the presence of a catalytic amount of aluminum chloride or aluminum bromide.

18. A process according to claim 1, wherein the temperature is between 110° and 200° C.

19. A process according to claim 1, wherein the proportion by weight of noble metal, relative to the compound of formula (I), is between 0.1 and 5%.

20. A process according to claim 1 for the preparation of 3,5-dichloroaniline, wherein: Y is the hydrogen or oxygen atom, X' and X" are the chlorine atom and R', R" and R''' are the hydrogen atom or the chlorine atom, at least one of them being the chlorine atom;

the reaction medium only contains a liquid phase, except for the catalyst based on a noble metal;
said at least one Lewis acid is present in a molar ratio, relative to the starting nitrogen-containing and chlorine-containing benzene derivative, between 0.01 and 0.5; and
the reaction is carried out at a total pressure not greater than about 21 bars and a temperature between 90° and 200° C.

* * * * *